United States Patent [19]

Reddy

[11] Patent Number: 4,993,431
[45] Date of Patent: Feb. 19, 1991

[54] PROPHYLACTIC DEVICE AND METHOD OF MANUFACTURE

[76] Inventor: Alla V. K. Reddy, 1042 Jade Dr., Hanna, Wyo. 82327

[21] Appl. No.: 571,323

[22] Filed: Aug. 22, 1990

Related U.S. Application Data

[63] Continuation of Ser. No. 293,993, Jan. 6, 1989, abandoned.

[51] Int. Cl.$^5$ ............................. A61F 6/02; A61F 6/06
[52] U.S. Cl. ...................................... 128/830; 128/842; 128/918
[58] Field of Search ............... 128/830, 832, 842, 844, 128/918; 604/349-352

[56] References Cited

U.S. PATENT DOCUMENTS

| | | | |
|---|---|---|---|
| 2,591,783 | 4/1952 | Craddock | 128/842 |
| 3,536,066 | 10/1970 | Ludwig | 128/830 |
| 4,664,104 | 5/1987 | Jaicks | 128/830 |
| 4,872,462 | 10/1989 | Salz et al. | 128/842 |
| 4,875,490 | 10/1989 | Quiroz | 128/830 |

FOREIGN PATENT DOCUMENTS

| | | | |
|---|---|---|---|
| 1158507 | 12/1983 | Canada | 604/349 |
| 3644344 | 7/1988 | Fed. Rep. of Germany | 128/830 |
| 117234 | 10/1926 | Switzerland | 604/349 |

*Primary Examiner*—Robert A. Hafer
*Assistant Examiner*—Kevin G. Rooney
*Attorney, Agent, or Firm*—John C. Evans

[57] ABSTRACT

A prophylactic device has a planar portion that is configured to cover the perineum of the user to prevent the exchange of bodily fluids between the user and a partner. The planar portion includes a pair of spaced integrally formed, adjustably positionable thigh bands located in spaced parallelism on either side of the planar portion. A leg opening is formed between each of the thigh bands and the planar portion to accommodate the legs of a user. The bands elastically shape to the user to prevent slippage of the planar portion from an overlying conformed relationship with the perineum of a user. The planar portion includes a pouch of generally circular cross-section throughout its length for insertion into a bodily orifice. A method for manufacturing the aforesaid prophylactic device includes the steps of providing a form with a base and a shaft of circular cross-section with its root connected to the base by sloping surfaces. The method further includes the step of dipping the form to cover the base and shaft with a single layer of elastic curable material and to form a thicker layer of the same material in the inner and outer recesses.

6 Claims, 4 Drawing Sheets

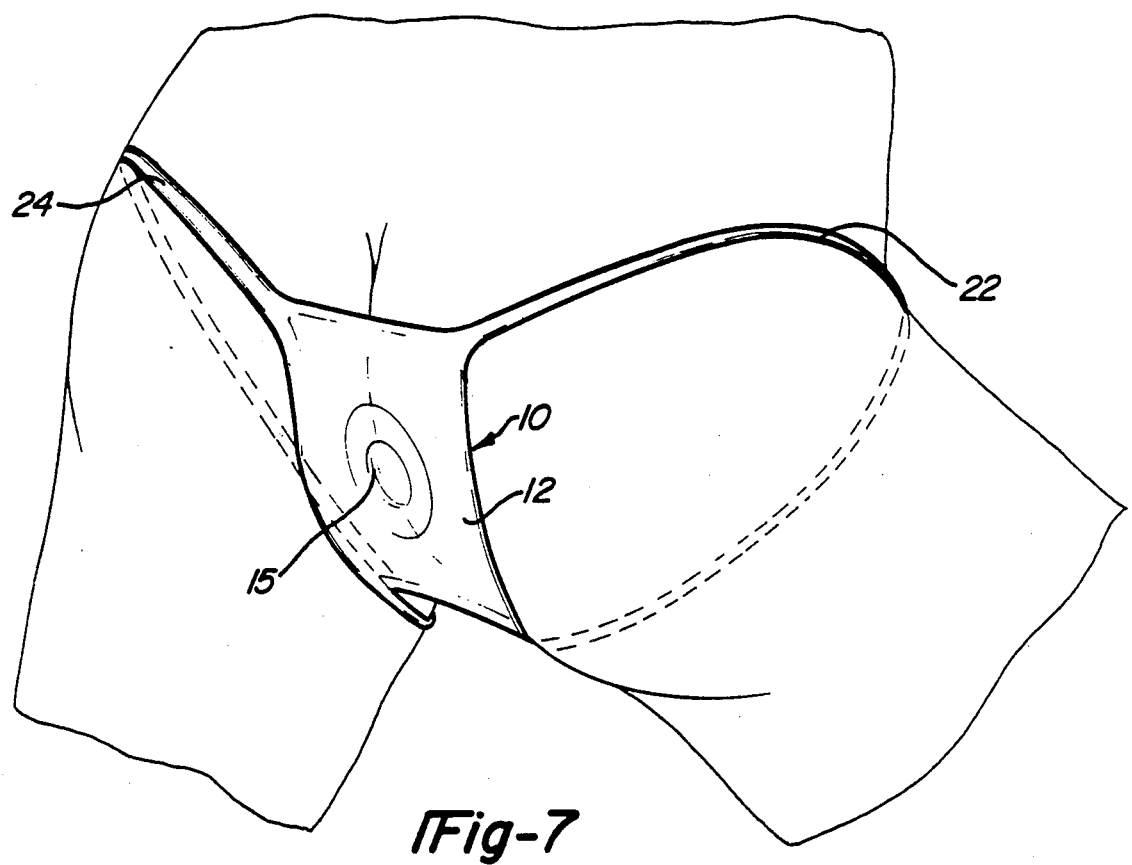
*Fig-7*
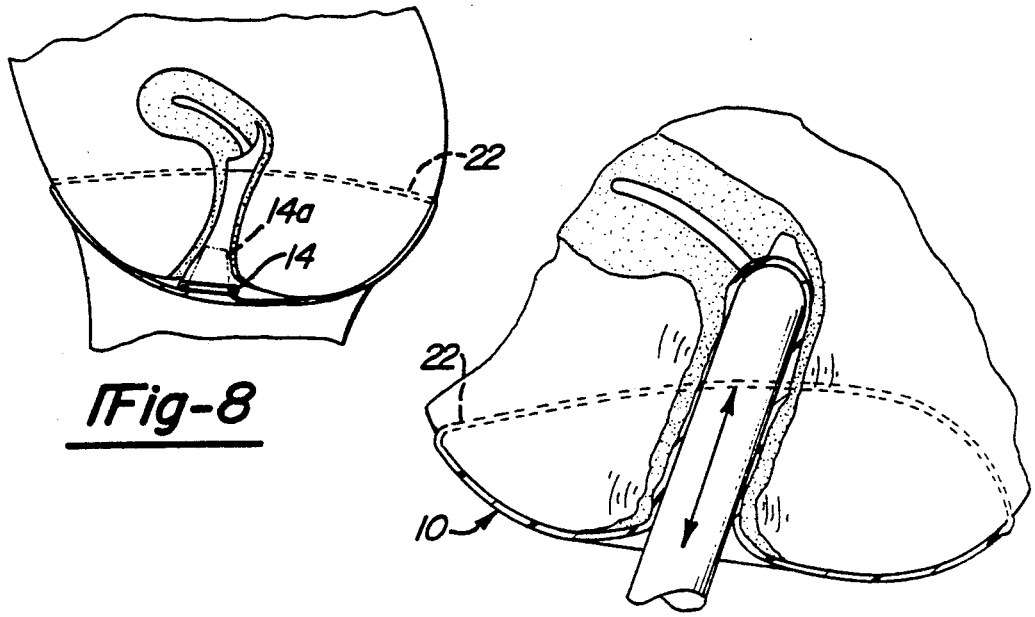
*Fig-8*  *Fig-8A*

PROPHYLACTIC DEVICE AND METHOD OF MANUFACTURE

This is a continuation of application Ser. No. 293,993, filed on Jan. 6, 1989, now abandoned.

FIELD OF THE INVENTION

This invention relates to prophylactic devices having a portion thereon conforming to the perineum region of a user to prevent the exchange of bodily fluids between the user and a partner so as to prevent the transmission of venereal diseases and AIDS and to a method and apparatus for manufacture thereof.

BACKGROUND OF THE INVENTION

With the widespread prevalence of venereal disease and the growing occurrence of AIDS (acquired immune deficiency syndrome), there is an increasing need for effective means to prevent the transmission of such diseases through sexual contact and resultant exchange of bodily fluids between a user and the user's partner.

Heretofore, conventional means for preventing the transmission of such bodily fluids and exposure to such diseases because of bodily contact have included the use of condoms, diaphragms, jells, creams and the like.

Additionally, there have been proposals to provide female prophylactic devices which can be worn by a female prior to use and disposed of following use. While such conventional and proposed devices are suitable for their intended purpose, it has been found that they are not totally effective for various reasons.

One example of a prior prophylactic device for use by females is that set forth in U. S. Pat. No. 3,536,066. The '066 patent shows a pant styled garment having a bellows configured pouch thereon which is located on the exterior of the pant. The bellows is preinsertable into the vaginal canal of a female prior to use. After the bellows is inserted, convolutions therein are extended to provide for extension of the bellows to accommodate an erected penis during use of the contraceptive device. The device requires preinsertion of a segment of the bellows and does not include means for piloting a large pouchlike member into a vaginal canal. Furthermore, the garment portions of the device are formed from rubber material which is configured to contact a large portion of the waist region of the user as well as the buttocks and hip regions of a user so as to cause possible irritation and discomfort when worn for substantial periods of time prior to use.

U. S. Pat. Des. No. 254,808 to Meldahl discloses a device for use as a male contraceptive. While the contraceptive has a larger diameter than typical condoms, it does not include a portion thereon which will serve as a shield that will conform to the perineum of a user of the device to prevent the passage of bodily fluids between a user and a partner. There are no straps to hold the device in place.

German Patentschrifft No. 210,143 (1909) discloses a female contraceptive device having a pouch that includes a generally circular collar on the other end thereof. There is no suggestion to provide a portion of the device that will cover and conform to the full perineum region of a user. Furthermore, there is no suggestion of how to hold the device in place during use.

U.S. Pat. No. 4,735,621 likewise shows a thin walled, condomlike, tubular protective device for insertion into a vaginal canal. It includes a resilient ring on one end thereof to anchor the device in the vaginal canal. The '621 patent does not provide a portion thereon which is adapted to conform to the full extent of the perineum region of a user. Furthermore, the device requires hand insertion to set the internal anchor and does not suggest how to prevent the device from slipping with respect to the perineum region to avoid exposing the user to exchange of bodily fluids through lesions on the perineum of either the user or the user's partner.

The aforesaid devices are either uncomfortable garment type devices or are devices which can slip from a desired seated relationship during use to cause undesirable exposure of the user to the exchange of bodily fluids between the user and the user's partner.

SUMMARY OF THE PRESENT INVENTION

In accordance with the present invention, a prophylactic device is provided which can be worn by either a female user or a male user to prevent the transmission of disease and/or sperm during sexual intercourse, which has a segment on the device which will secure a perineum portion of the device to the user and retain it thereon without slippage during use wherein a pouch portion formed on the perineum covering portion is located interiorly of a body orifice of the user. One feature of the invention is to provide a prophylactic device which includes a first planar portion configured to be conformed to and to completely cover the perineum of the user. The first planar portion includes a pair of spaced elastic bands thereon located in spaced parallel relationship and adapted to be stretched to form a pair of spaced leg openings through which a user's legs can be inserted to conform the first portion to the perineum of the user. The elastic bands stretch around the thighs of the user and apply pressure thereon to provide an anchor against slippage of the first portion from its conformed relationship with the perineum to thereby assure bodily coverage during intercourse between the user and the user's partner.

Another feature of the invention is the provision of an elongated hollow pouch extending from the planar portion. It has a rounded end closure which is integrally joined to prevent the escape of fluids from the pouch during use. Inclined surfaces join the pouch to the planar portion to define an opening into the pouch. The resultant shape is easily fabricated and easily conformed to a user and to the user's partner.

Another feature of the invention is to provide a prophylactic device with a planar portion, leg bands, and pouch formed of a layer of elastic material and wherein the leg bands are placed about the legs of a user to conform the planar portion thereof into overlying relationship with the user's perineum while aligning the pouch portion thereof into overlying relationship with a bodily cavity of a user.

The prophylactic device of the prevent invention can be worn by either a female person or a male person and will provide protection on either person by disposing the planar portion thereof in conformed and covering relationship to the perineum of the user while locating the pouch either in alignment with the vaginal canal of a female person when used by a female person or in alignment with the anal canal of a male person when used by a male person merely by changing the position of the elastic bands on the thighs of the user.

In either case, the universal prophylactic device is initially configured to have the pouch segment thereof rolled and initially disposed substantially in the same plane as the first planar portion of the prophylactic device. The rolled pouch has a first telescopingly extended pilot for entry into a bodily orifice of either a male or a female person.

The pouch is extensible inwardly of the body orifice of either a male or a female person upon initial extension of the pouch by the pilot formed on the pouch during initial disposition. Thereafter the pouch is extended by unrolling a telescoped portion of the pouch into the body cavity during penetration of an erected penis therein to define an extended pouch configuration. The walls of the pouch are deformable apart from one another to provide an extended opening for passage of an erected penis through the pouch portion as it is extended into the bodily orifice of a user.

Another feature of the present invention is to provide such a unisex prophylactic device having integral elastic bands which will stretch and adjustably position on a user's thighs to conform to either a female or male person to locate the planar portion thereon to fully cover and conform to the perineum region of either a male or a female user.

Another feature of the present invention is to provide elastic bands of the type set forth in the last mentioned feature which will exert a sufficient band pressure on the user's legs to prevent the perineum covering portion from slipping from the perineum during use.

Still another feature of the present invention is to manufacture prophylactic devices of the type having the features set forth above by the steps of providing a form having a base and a shaft extending from a first planar surface of the base; the base having a pair of spaced narrow elongated segments thereon and the step of placing the form into a dipping bath of latex or other suitable material to form a single layer of elastic material on the base and shaft and thereafter curing the latex material or other suitable material to form a prophylactic device having integrally formed bands thereon which will readily stretch with respect to the user's body to conform the device to the user so as to prevent slipping from a conformed position on the user.

Other advantages of the device of this invention will become more apparent from the following detailed description.

BRIEF DESCRIPTION OF THE DRAWINGS

The invention is described in more detail hereafter with reference to the accompanying drawings wherein:

FIG. 7 is a perspective view of the anatomically configured unisex embodiment of the invention supported on a male user;

FIGS. 8 and 8A are sectional views taken along line 8—8 of FIG. 6 looking in the direction of the arrows to show the present invention positioned at different points in the vaginal canal of a female user;

DETAILED DESCRIPTION OF THE INVENTION

Figure 1:
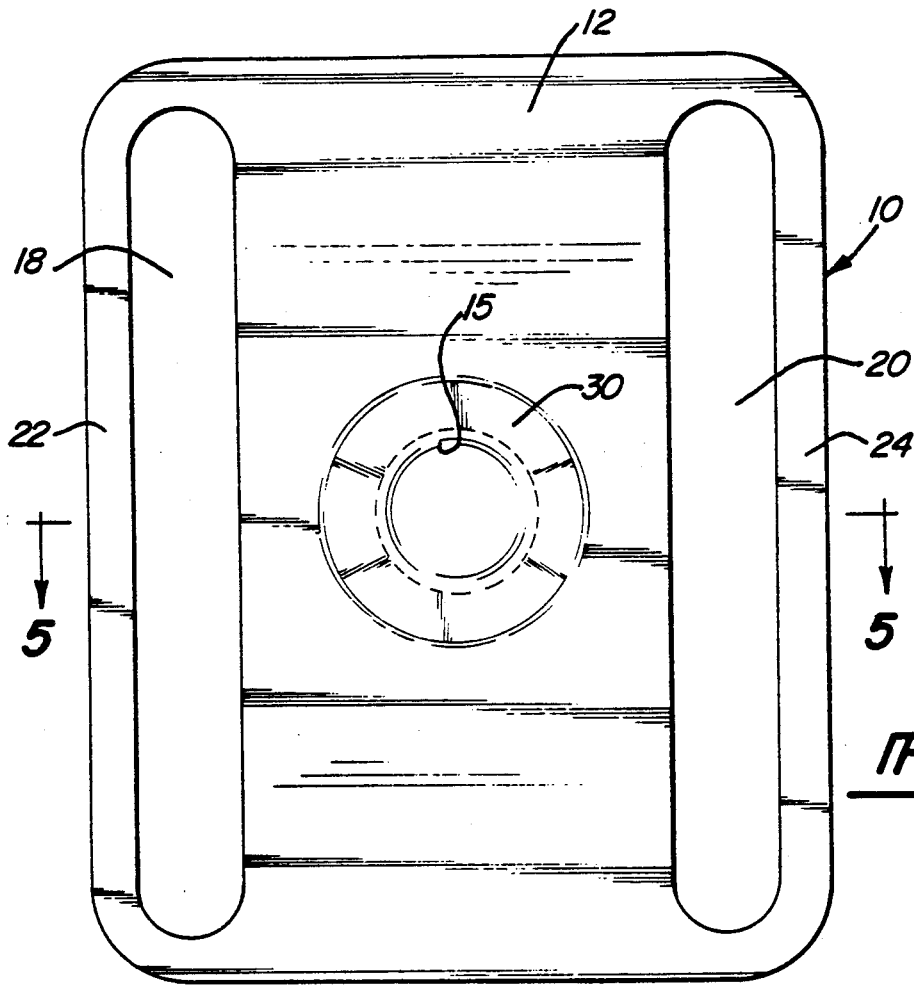
FIG. 1 is a front elevational view of a reinforced prophylactic device of the present invention.
Figure 2:
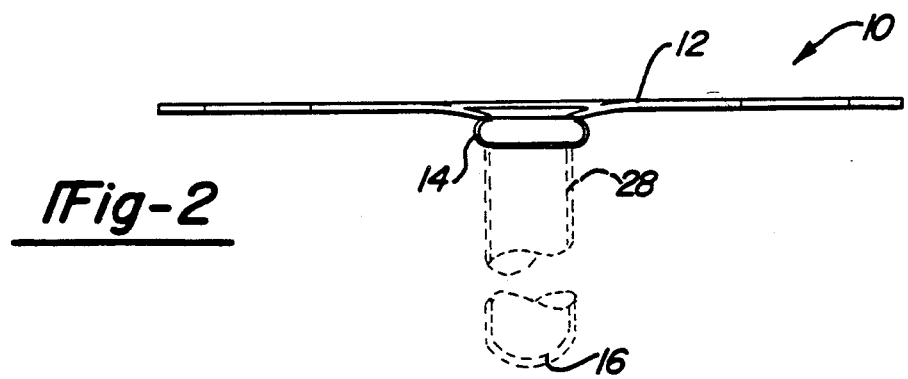
FIG. 2 is an end elevational view of the reinforced prophylactic device shown in FIG. 1.
Figure 3:
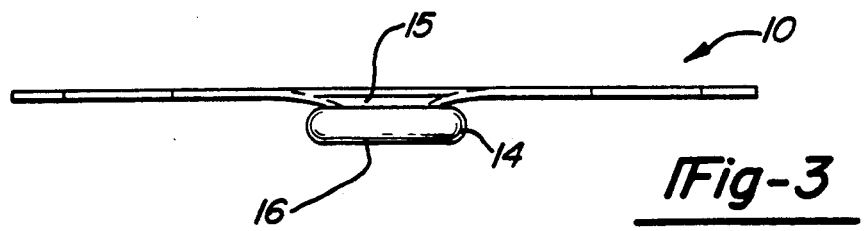
FIG. 3 is a side elevational view of the reinforced prophylactic device shown in FIG. 1.

FIGS. 1-3 show an anatomically configured, unisex prophylactic device 10 which can be universally used by either male or female persons to protect against transmission of disease, including but not limited to those discussed with reference to the cited background art.

The device 10 includes a first planar portion 12 that serves as a shield which will cover and generally conform to the full surface extent of the perineum region of either a male or a female user. The planar portion 12 is integrally joined with an expandable pouch 14 that is shown in a rolled position (FIGS. 1-5). A rounded end closure 16 of the rolled pouch 14 is located below an entrance opening 15 to the pouch 14. A rectangular outer segment 11 of the device surrounds the rectangular portion 12 thereof. A pair of narrow, elongated leg openings 18, 20 are directed through the device 10 on either side of the planar portion 12 to separate the planar portion 12 from a pair of spaced parallel elastic bands 22, 24 in the retangular outer segment 11. The rectangular outer segment 11 also includes upper and lower segments 23, 25 which together with the bands 22, 24 define an outer peripheral segment 26 of device 10. The elastic bands 22, 24 have a width narrower than the width of the undeformed leg openings 18, 20. Additionally, the device 10 includes an outer peripheral segment 26 of reinforcing material integrally formed with and of the same material as the rest of the device 10. The planar portion 12 has side edges 12a and 12b and it his end edges 12c and 12d. The side edges 12a, 12b are in spaced parallelism to the bands 22, 24 and the end edges 12c and 12d are integrally connected to the upper and lower segments 23, 25 of the rectangular portion 12. As will be set-forth below the planar portion 12 has a major dimension between the end edges 12c and 12d and a minor dimension between the side edges 12a and 12b. As will be described in more detail the dimensions are selected to cover the perineum of either a female user or a male user.

Figure 4:
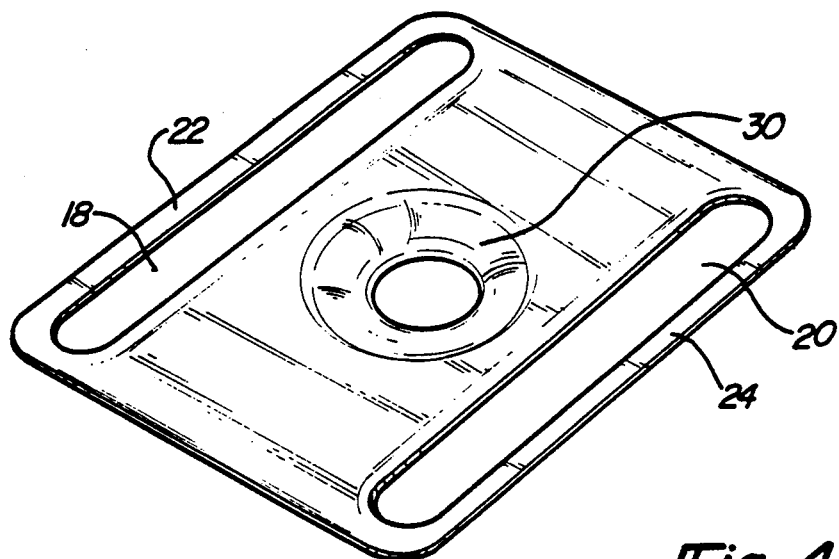
FIG. 4 is a perspective view of the embodiment of FIG. 1.
Figure 5:
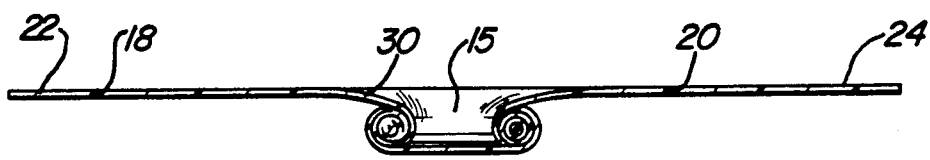
FIG. 5 is an enlarged cross-sectional view taken along the line 5—5 of FIG. 1 looking in the direction of the arrows.

In accordance with the present invention, the material of the device 10 is an elastic material such as cured latex which will stretch to conform to the body of a user. More particularly, and as best seen in FIG. 4, the pouch 14 includes a circular side wall 28 to form a resultant pouch that is hollow throughout its length and having the opening 15 at one end of the pouch and the rounded end closure 16 at the other end. The pouch 14 will trap any fluids directed thereto during use of the prophylactic device.

Figure 6:
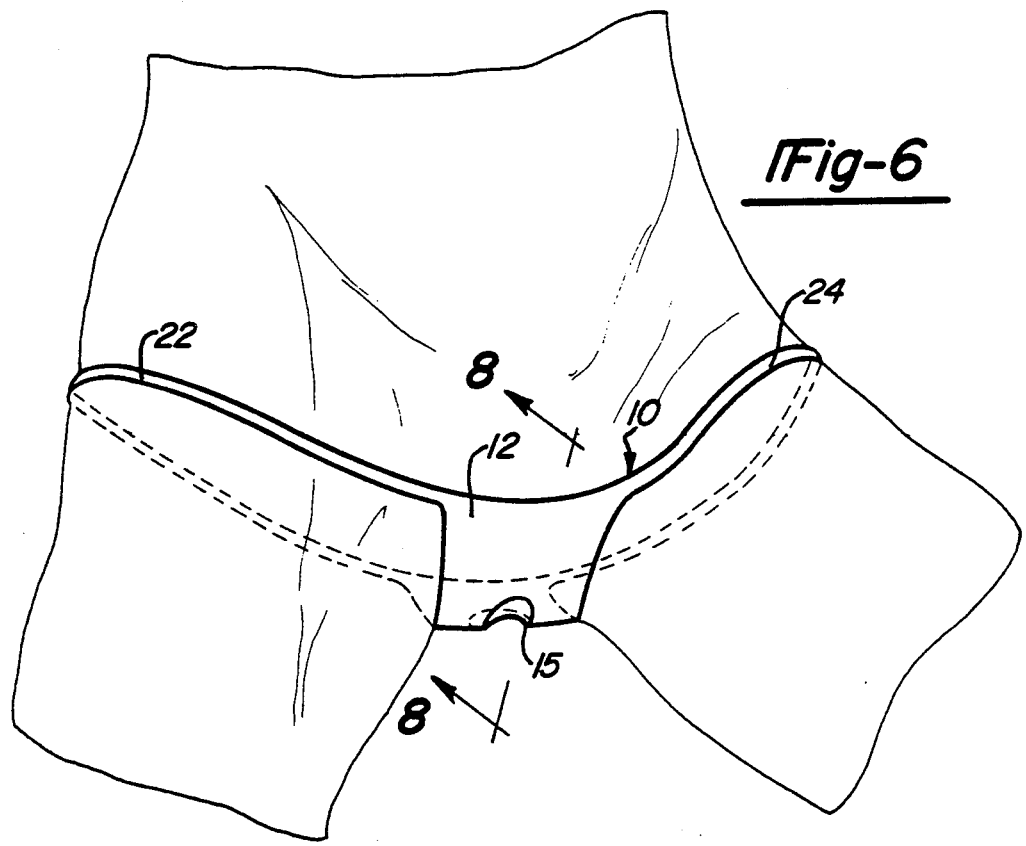
FIG. 6 is a perspective view of an anatomically configured unisex embodiment of the invention supported on a female user.

As shown in FIG. 6, the prophylactic device 10, when used by a female user, has the elastic bands 22, 24 adjusted on and stretched around the thighs of a user to place the planar portion 12 over the perineum region of a female user from the upper region of the pubic area of the female to the perineum in the region of the anal orifice of the female user. In this position, the bands 22, 24 are located high on the thighs as shown in FIG. 6. The bands 22, 24 remain narrow and the leg holes 18, 20 are widened to the width of the user's thigh dimensions. The planar portion 12 of the device 10 is positioned to fully cover the perineum of the female user as the opening 15 of the pouch 14 is aligned with the entrance to the vaginal canal of the female user. The bands 22, 24 elastically grip the outer surface of the thighs of the user to provide a pressure thereon which serves as an anchor against slippage of the perineum covering planar portion 12 of the device during use. Furthermore, the narrow bands 22, 24 only cover a limited surface of the user's body while securing the planar portion 12 in place. Thus, the prophylactic device 10 contacts minimal surfaces on the user's body while anchored in place thereon.

The retention pressure of the bands 22, 24 will hold the perineum covering portion 12 in place and thereby will prevent the device 10 from slipping because of movement of the pouch 14 with respect to the vaginal canal either during initial disposition or during coitus.

Another feature of the present invention is that the wall 28 of the pouch 14 will stretch to accommodate the shape of the bodily cavity into which it is inserted during use. Moreover, the wall 28 will readily loosely fit over an erected penis inserted into the pouch 14.

Another feature of the present invention is the provision of an inclined entrance wall 30 at the opening 15 to the pouch 14. The inclined entrance wall 30 provides a smooth transition from the planar portion 12 to the wall 28 of the pouch 14.

Figure 11:
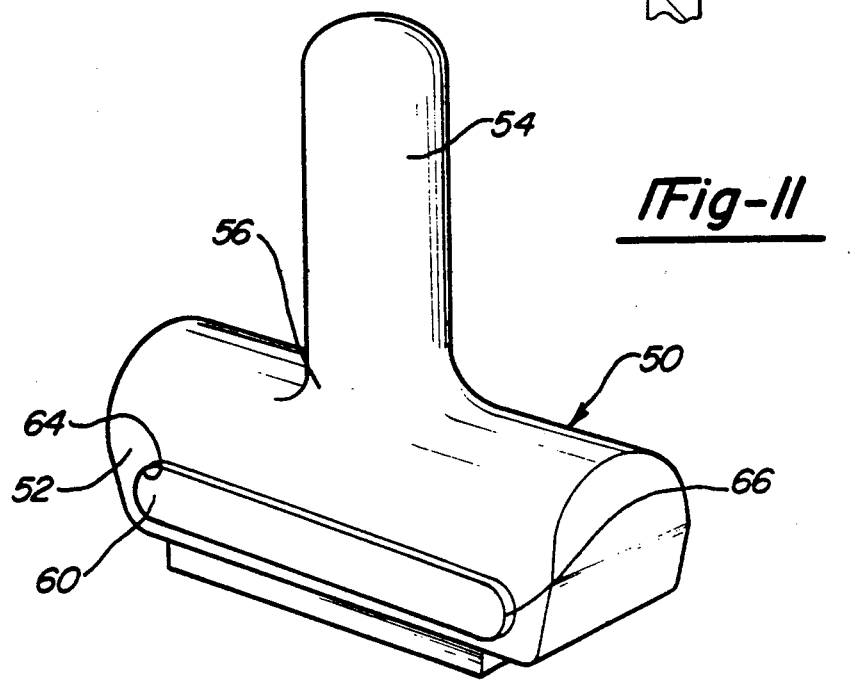
FIG. 11 is a perspective view of a form for making the prophylactic device of the present invention.

FIG. 11 illustrates a form 50 having a base 52 and a shaft 54 with its root forming a smooth circular fillet connection 56 to the base 52. The fillet 56 forms a transition surface for flow of dipping composition across the form surfaces and also enable a dip formed device to be easily removed from a form covered with known release agents.

The form 50 further includes a pair of narrow, elongated raised segments 60, 62 on either side thereof along the length of the form 50. Each of the segments 60, 62 includes opposite semicircular end portions 64, 66.

In accordance with the process of the present invention, a form 50 is provided having the form as described with reference to FIG. 11. It is located above an open ended container that is filled with synthetic or latex material of a composition which will result in desired resilient stretch properties in prophylactic device 10.

The form 50 is connected to a suitable carriage means which will direct the form, shaft first, into the latex material to cover surfaces of the shaft 54 and curved surfaces 68, 70 of base 52. A resultant build up of material occurs on the form 50. The form 50 is tilted or otherwise moved back and forth to distribute the latex material evenly (leveled) across the surfaces of the form and to fill the recesses around raised segments 60, 62.

Excess dipping material is allowed to flow across the form surfaces and then the form is directed through conventional heating means to dry and cure the latex mateial on the form.

Figure 9:
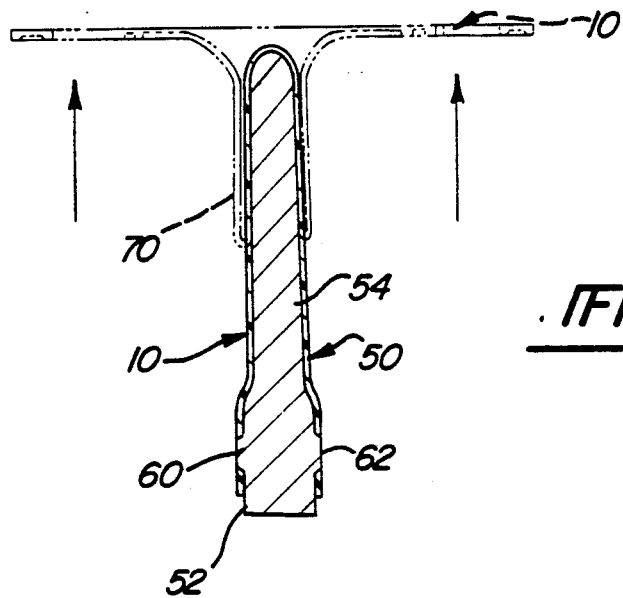
FIG. 9 is a cross-sectional view showing a prophylactic device formed on the form of FIG. 11.

A resultant prophylactic device 10 is shown on the form 50 in FIG. 9. FIG. 9 shows how the device 10 is stripped from the form 50 by moving the formed material upwardly with respect to the form 50 to form a double walled, telescoped section 70 in the pouch 14 which can then be rolled upon itself.

Figure 10:
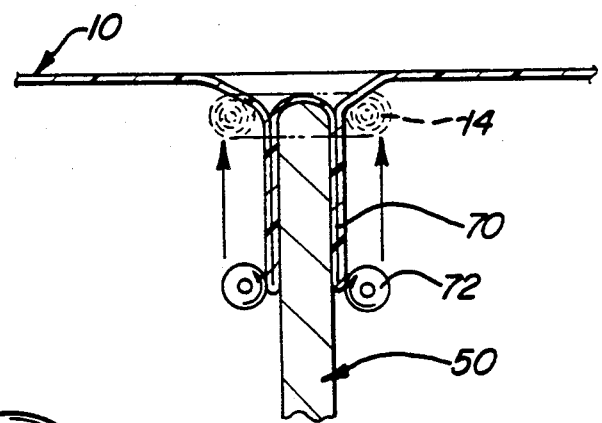
FIG. 10 is an elevational view of the form diagrammatically showing apparatus for rolling the prophylactic device for packaging.

Rollers 72 engage the double walled telescoped segment 70 as shown in FIG. 10 to remove the deposited material from the form 50 to form a resultant prophylactic device 10 with a rolled pouch 14.

Another feature of the resultant prophylactic device 10 is that the inclined surface 30 forms a piloted entrance to the inlet opening 15 of the pouch 14 to apply a force through the opening 15 and against the end closure 16 for moving the rolled pouch 14 from the planar portion 12 of the prophylactic device 10. Initially, the rolled pouch 14 extends to the double wall telescoped shape to define a pilot portion 14a. One aspect of the present invention is that the rolled double walled portion 102 is arranged so that the pouch 14 will initially unroll to form the pilot portion 14a shown in dotted line configuration in FIG. 8 as the pouch first enters into a body cavity. The pilot portion 14a is carried by further entry into a body cavity by unrolling the rolled double wall portion 70 until the pouch is fully disposed as shown in FIG. 8A.

The prophylactic device can have various sizes and wall thicknesses in accordance with the invention. For example, the pouch 14 may have a length in the range of 1 to 10 inches, preferably about 4 to 6 inches and the maximum diameter of the wall 28 will vary from $1\frac{1}{2}$ to 4 inches. While the pouch 14 is shown as having a uniform circular cross-section throughout its length, the cross-section of the shape can vary along the length. The thickness of the wall material of the prophylactic device may also vary. For example, it can be as thin as 0.0005 inches or as thick as 0.1 inches. Preferably the wall thickness will be in the range of about 0.001 to 0.005 inches. While the material for forming the deposited material is preferably made of elastic impermeable substances such as natural rubber (e.g., latex), synthetic rubber (e.g., silicon rubber), or polyurethane. Other useful materials include nonelastic material such as various plastics including polyvinyl chloride and polyethylene.

In the specific illustration of FIGS. 1 through 5, the prophylactic device 10 is made of latex material. The wall thickness of the unreinforced portions of the prophylactic device 10 is 0.0035 inches and the wall thickness of the double layer reinforcing portions are slightly thicker.

The overall unstretched width of the planar portion 12 of the prophylactic device 10 is 6.5 inches and the overall length of the planar portion 12 is 8 inches. The leg openings 80, 20 have an unstretched width of 0.875 inches and a length of $7\frac{1}{4}$ inches.

The unstretched dimensions of the generally planar segment 12 includes a width of $3\frac{1}{2}$ inches and a length of 7.75 inches. The length of the pouch is in the order of 6 inches and its diameter is approximately 2 inches.

The aforesaid dimensions are cited for illustrative purposes only, with it being understood that dimensions are selected so that the prophylactic device 10 can be configured to anatomically relate to the perineum region of either a female user of the prophylactic device 10 or a male user of the device. In either case, once the prophylactic device 10 is located over the perineum of the user, the pouch 14 can be rolled from its stored position in close spaced relationship with the plane of the planar portion 12 to an extended position within a body cavity of a user.

When the device is used by a male user, as shown in FIG. 7, the segment 12 will cover the perineum region from the general area of the user's crotch to a region above the anal cavity in the vicinity of the coccyx region of the male user. In this arrangement, the pouch 14 will be positioned in general alignment with an anal passage way. The pouch 14 is extendable therein to prevent the exchange of bodily fluids during use of the prophylactic device while shielding the user and partner from bodily fluid exchange at the perineum region of the user. As shown in FIG. 7, in this case, the universally adaptable prophylactic device 10 has its elastic bands disposed on the user's buttocks and thighs to cover the perineum from the user's genitals to the coccyx region.

While the best mode for carrying out the invention has herein been described in detail, those familiar with the art to which this invention relates will recognize various alternative designs and embodiments for practicing the invention as defined by the following claims.

What is claimed is:

1. An anatomically configured unisex prophylactic device formed of elastic impermeable material for preventing the exchange of bodily fluids between either a male or female user and partner of the user comprising:
   a flat planar rectangular shield portion having spaced parallel side edges, spaced parallel end edges and a major dimension and a minor dimension; said major dimension having a length which covers a female user's perineum from the pubic region to anal region and a length which covers a male user's perineum from the user's crotch to the coccyx region of a male user;
   a pouch connected to said planar portion and extendable therefrom and adapted to be inserted into a bodily cavity of either a male or female user when said planar portion is disposed to cover either a female user's perineum from the pubic region to the anal region or to cover a male user's perineum from the user's crotch to the coccyx region;
   a rectangular outer segment located in surrounding relationship to said flat planar portion and having upper and lower segments formed integrally of said spaced parallel end edges of said flat planar rectangular shield portion; said rectangular outer segment further including two spaced band segments located in spaced parallelism with said side edges and extending parallel thereto through a distance equal to that of said major dimension;
   said band segments and said side edges forming narrow elongated leg openings having a length equal to said major dimension and an unstretched width that is less than one inch;
   said band segments being stretchable with respect to said side edges of said shield portion to be disposed on the thighs of either a male or female user for locating said pouch in alignment with either a vaginal opening of a female user or an anal opening of a male user.

2. In the prophylactic device of claim 1,
   said pouch having a uniform cross-section throughout its length and wall means to form a pouch opening;
   means for closing the end of said pouch to prevent the escape of fluids therefrom when said pouch is inserted into the bodily cavity of the user; and
   said pouch, planar portion and said bands having an elasticity to permit conforming the planar portion to the perineum of the user, to conform the bands to the legs of the user to prevent the planar portion from slipping from its conformed relationship on the perineum of a user and to provide for stretch of the pouch with respect to the conformed planar portion as it is inserted into a bodily cavity of the user.

3. In the prophylactic device of claim 1, said bands having a length and a width and elasticity which will produce a band pressure around the thigh of a user to cause said bands to prevent the planar portion from slipping from the user during use.

4. In the prophylactic device of claim 2, said bands having a length and a width and elasticity which will produce a band pressure around the thigh of a user to cause said bands to prevent the planar portion from slipping from the user during use.

5. In the prophylactic device of claim 1, said bands having a width narrower than the width of said leg openings throughout the length of said bands.

6. In the prophylactic device of claim 2, said bands having a width narrower than the width of said leg openings throughout the length of said bands.

* * * * *